United States Patent
Akiyama et al.

(10) Patent No.: US 10,578,560 B2
(45) Date of Patent: Mar. 3, 2020

(54) INSPECTION APPARATUS AND METHOD FOR DETECTING FALSE DEFECTS

(75) Inventors: Hiroteru Akiyama, Kanagawa (JP); Ikunao Isomura, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 355 days.

(21) Appl. No.: 13/440,080

(22) Filed: Apr. 5, 2012

(65) Prior Publication Data

US 2012/0307043 A1 Dec. 6, 2012

(30) Foreign Application Priority Data

May 31, 2011 (JP) .................. 2011-122498

(51) Int. Cl.
*H04N 7/18* (2006.01)
*G01N 21/956* (2006.01)

(52) U.S. Cl.
CPC .......... *G01N 21/95607* (2013.01); *G01N 2021/95615* (2013.01)

(58) Field of Classification Search
USPC .................................. 382/144, 145
See application file for complete search history.

(56) References Cited

U.S. PATENT DOCUMENTS

| | | | | |
|---|---|---|---|---|
| 5,390,264 A | * | 2/1995 | Ishihara | G06T 5/20 382/260 |
| 5,710,840 A | * | 1/1998 | Hideshima | G06T 5/20 382/254 |
| 5,805,216 A | * | 9/1998 | Tabei | H04N 5/367 348/241 |
| 5,960,106 A | * | 9/1999 | Tsuchiya | G06T 7/0006 382/144 |
| 6,076,465 A | * | 6/2000 | Vacca | G01N 21/95607 101/481 |

(Continued)

FOREIGN PATENT DOCUMENTS

| | | |
|---|---|---|
| JP | 7-318506 | 12/1995 |
| JP | 2008011630 A * | 1/2008 |
| JP | 2008-112178 | 5/2008 |

OTHER PUBLICATIONS

U.S. Appl. No. 13/768,392, filed Feb. 15, 2013, Inoue, et al.

(Continued)

*Primary Examiner* — Jayanti K Patel
*Assistant Examiner* — Stefan Gadomski
(74) *Attorney, Agent, or Firm* — Oblon, McClelland, Maier & Neustadt, L.L.P.

(57) ABSTRACT

An inspection apparatus and method comprising a unit for acquiring an optical image of an object to be inspected by irradiating the object with light, wherein the unit includes a line sensor comprising a plurality of sensors linearly arranged in a row, a generating unit for generating a reference image from design data of the object to be inspected, a comparing unit for comparing the optical image with the reference image, a unit for storing data of three lines acquired by the line sensor, and calculating differences between a gradation value of a pixel on a center line and each gradation value of the eight pixels adjacent to the pixel determining if the pixel is a defect if all of the eight differences of the adjacent pixels are more than a predetermined threshold.

2 Claims, 10 Drawing Sheets

(56) References Cited

U.S. PATENT DOCUMENTS

| | | | |
|---|---|---|---|
| 6,396,943 B2* | 5/2002 | Yamashita | G06T 7/001 382/144 |
| 6,411,377 B1* | 6/2002 | Noguchi | B82Y 15/00 356/237.4 |
| 6,724,929 B1* | 4/2004 | Matsuoka | G06T 7/001 382/145 |
| 6,978,045 B1* | 12/2005 | Hashimoto | G06K 15/02 382/199 |
| 7,032,208 B2* | 4/2006 | Yamashita | G01N 21/95607 356/237.2 |
| 7,359,546 B2* | 4/2008 | Sugihara et al. | 382/145 |
| 7,369,165 B2* | 5/2008 | Bosco et al. | 348/272 |
| 7,542,082 B2* | 6/2009 | Tajima | H04N 5/3675 348/241 |
| 7,751,610 B2* | 7/2010 | Takarada | G06K 9/6212 382/144 |
| 8,260,031 B2* | 9/2012 | Yamashita | G06T 7/001 382/144 |
| 8,571,301 B2* | 10/2013 | Sonoura | G01N 21/956 382/145 |
| 2003/0020835 A1* | 1/2003 | Petrescu | H04N 5/14 348/625 |
| 2003/0031356 A1* | 2/2003 | Sasa | G01N 21/95607 382/145 |
| 2004/0051798 A1* | 3/2004 | Kakarala | H04N 5/367 348/246 |
| 2005/0147287 A1* | 7/2005 | Sakai | G01N 21/9501 382/141 |
| 2006/0002604 A1* | 1/2006 | Sakai | G06T 7/001 382/141 |
| 2006/0012694 A1* | 1/2006 | Yoneda | H04N 5/3675 348/246 |
| 2007/0019858 A1* | 1/2007 | Shimura | G06T 7/001 382/149 |
| 2007/0177787 A1* | 8/2007 | Maeda | G06K 9/00557 382/141 |
| 2007/0257997 A1 | 11/2007 | Tanizoe | |
| 2008/0101686 A1* | 5/2008 | Sali | G01N 21/95607 382/149 |
| 2009/0041334 A1* | 2/2009 | Nagano | G06K 9/00 382/149 |
| 2009/0080003 A1* | 3/2009 | Murakami | H04N 1/58 358/1.9 |
| 2009/0238446 A1* | 9/2009 | Kataoka | G03F 1/84 382/152 |
| 2009/0245620 A1* | 10/2009 | Joo | G06K 9/00 382/145 |
| 2009/0303323 A1* | 12/2009 | Yoshikawa | G01N 21/95607 348/92 |
| 2009/0304262 A1* | 12/2009 | Harabe | G01N 21/95607 382/152 |
| 2010/0277478 A1* | 11/2010 | Ihm | G06T 15/503 345/426 |
| 2010/0322509 A1* | 12/2010 | Shimizu | G06T 5/002 382/162 |
| 2011/0091099 A1 | 4/2011 | Akiyama | |
| 2011/0158515 A1* | 6/2011 | Chuang | H04N 1/58 382/163 |
| 2011/0187935 A1* | 8/2011 | Omori | H04N 5/21 348/625 |
| 2011/0194753 A1* | 8/2011 | Kamiyama | G01N 21/8851 382/149 |
| 2011/0292998 A1* | 12/2011 | Ohgose | H04N 19/176 375/240.08 |
| 2012/0026316 A1* | 2/2012 | Nagahama | G01N 21/95607 348/92 |
| 2013/0236096 A1* | 9/2013 | Cerundolo | G06T 5/20 382/167 |

OTHER PUBLICATIONS

U.S. Appl. No. 13/792,364, filed Mar. 11, 2013, Inoue, et al.
U.S. Appl. No. 12/902,622, filed Oct. 12, 2010, 2011-0091099, Akiyama.

* cited by examiner

Fig. 2

| 110 | 100 | 110 |
|-----|-----|-----|
| 110 | 150 | 110 |
| 100 | 100 | 100 |

Fig. 3

| 210 | 110 | 90 |
|-----|-----|-----|
| 210 | 150 | 90 |
| 200 | 100 | 80 |

| 100 | 100 | 100 | 100 | 100 | 100 | 100 |
|-----|-----|-----|-----|-----|-----|-----|
| 100 | 110 | 110 | 110 | 110 | 110 | 100 |
| 100 | 110 | 120 | 120 | 120 | 110 | 100 |
| 100 | 110 | 120 | 140 | 120 | 110 | 100 |
| 100 | 110 | 120 | 120 | 120 | 110 | 100 |
| 100 | 110 | 110 | 110 | 110 | 110 | 100 |
| 100 | 100 | 100 | 100 | 100 | 100 | 100 |

Fig. 10

| 100 | 100 | 100 | 100 | 100 |
|---|---|---|---|---|
| 100 | 100 | 100 | 100 | 100 |
| 100 | 100 | 200 | 100 | 100 |
| 100 | 100 | 100 | 100 | 100 |
| 100 | 100 | 100 | 100 | 100 |

Fig. 11

INSPECTION APPARATUS AND METHOD FOR DETECTING FALSE DEFECTS

CROSS-REFERENCE TO THE RELATED APPLICATION

The entire disclosure of the Japanese Patent Application No. 2011-122498, filed on May 31, 2011 including specification, claims, drawings, and summary, on which the Convention priority of the present application is based, are incorporated herein in its entirety.

FIELD OF THE INVENTION

The present invention relates to an inspection apparatus and inspection method.

BACKGROUND

In recent years, as the levels of integration and capacity of large scale integrated circuits (LSIs) have increased, there has been a need to continue to reduce the width of the circuit patterns of semiconductor units. Semiconductor units are manufactured by a reduced projection exposure apparatus called a "stepper" using original artwork patterns with a circuit pattern formed thereon, these are called masks or reticles (hereinafter referred to collectively as masks). Specifically, a pattern on a mask is transferred to a wafer by exposure to light, thereby forming circuits on to the wafer. Masks used to transfer such fine circuit patterns to the wafer are manufactured by electron beam writing apparatuses, which can write micropatterns. Further, effort has been made to develop a laser beam writing apparatus, which uses a laser beam for writing. It should be noted that electron beam apparatuses are also used to directly write a circuit pattern on a wafer.

Incidentally, since the cost of manufacturing LSIs is very high, an improvement of yield is required to make the manufacture economically feasible. However, the dimensions of the patterns for LSI units, as typified by 1-gigabit class DRAMs (random access memories), are about to be scaled down from the order of submicrons to the order of nanometers. A major cause of loss in yield is due to defects of a mask pattern. Further, since there has been a decrease in the dimensions of LSI patterns formed on semiconductor wafers, the size of pattern defects to be detected is very small. Therefore, high inspection accuracy is required of mask inspection systems for detecting defects of transfer masks used in LSI manufacture.

One of the methods used for detecting defects is the die-to-database inspection method. In this method, an optical image of a pattern is compared with a reference image of the pattern made from design data inputted into an inspection apparatus. The design data is data converted from CAD data into a format that can be input into the inspection apparatus.

In a die-to-database inspection method, light is emitted from a light source, and the mask to be inspected is irradiated with this light through an optical system. The mask is mounted on a table, and this table is moved so that the emitted beam of light scans the surface of the mask. Light transmitted through or reflected from the mask is focused on an image sensor forming an image thereon. The optical image thus formed on the image sensor is sent to a comparing unit. The comparing unit compares the optical image measurement data with the reference image data in accordance with an appropriate algorithm, and if they are not identical, the mask is determined to have a defect (see Patent Document 1).

[Patent Document 1] Japanese laid-open Patent publication No. 2008-112178

In the defective inspection process, defects are displayed on a monitor based on the data created from the inspection result. The operator determines whether these defects are problematic and classifies the defects accordingly. More specifically, a comparison image is generated from the optical image and the reference image, and then the defects displayed in the comparison image are reviewed by the operator.

In the defective inspection process there is a possibility that a false defect is detected by the inspection apparatus. This false defect can extend the review time for the operator, it is therefore preferred to minimize the occurrence of these false defects.

One example of a false defect is white spot. This false defect is caused by cosmic rays.

An image sensor used on an inspection process is sensitive to the cosmic rays. As a few thousand electron-hole pairs are generated by one cosmic ray, multiple false defects occur in a position where a cosmic ray passes through an optical image. This image is referred to as a white spot, because it is brighter than the adjacent to the optical image. White spot can be confused with a true defect and therefore the white spot should be removed from the inspection result. It is difficult to shield the cosmic rays by use of, for example, a screen.

White spots are also known in astronomy. In astronomy white spot can be confused with a star, as one example. The white spot generates randomly in time and space, but the possibly that a white spot is generated several times at the same position is extremely low. Therefore in astronomy, images of the same object are acquired several times and then are compared with each other, thus the white spot can be removed.

However, it is difficult to apply the above method in an astronomy process to a white spot generated in the inspection process. The time taken for an inspection process is longer than the time taken to acquire information of a star, as one example. The work required for comparing images acquired by repeating the inspection process several times causes a significant decline in productivity. Further, there must be a limit to the amount of defect determination that can be correctly determined by an algorithm for defect inspection, that is, whether a defect is a false defect or not.

The present invention has been conceived in view of the above problem. Therefore, an object of this invention is to provide an inspection apparatus and an inspection method capable of improving the accuracy of the inspection process by removing white spot.

Other challenges and advantages of the present invention are apparent from the following description.

SUMMARY OF THE INVENTION

The present invention relates to an inspection apparatus and method comprising a unit for acquiring an optical image of an object to be inspected by irradiating the object with light.

The first embodiment comprising; an optical image acquiring unit for acquiring an optical image of an object to be inspected by irradiating the object with light, wherein the optical image acquiring unit includes a line sensor comprising a plurality of sensors linearly arranged in a row, a reference image generating unit for generating a reference image from design data of the object to be inspected, a comparing unit for comparing the optical image with the reference image, a false defect determining unit for storing data of three lines acquired by the line sensor, and calculating differences between a gradation value of a pixel on the center line and each gradation value of the eight pixels adjacent to the pixel determining the pixel as a defect if all of the eight differences are more than a first predetermined threshold.

Further to the first embodiment of this invention; an inspection apparatus wherein the false defect determining unit calculates an average of the gradation values of the eight adjacent pixels, and replaces the gradation value of the pixel with the average of the eight adjacent pixels.

Further to the first embodiment of this invention; an inspection apparatus wherein in the false defect determining unit, if a difference between the maximum and the minimum of the gradation values of the eight adjacent pixels is more than a second threshold, the pixel is not regarded as a false defect.

In the second embodiment of this invention, an inspection apparatus comprising; an optical image acquiring unit for acquiring an optical image of an object to be inspected by irradiating the object with light, a comparing unit configured to compare the optical images, a false defect determining unit for storing data of three lines acquired by the line sensor for calculating differences between a gradation value of a pixel on the center line and each gradation value of the eight pixels adjacent to the pixel and if all of the eight differences are more than a predetermined first threshold determining the pixel to be a defect.

Further to the second embodiment of this invention; an inspection apparatus wherein the false defect determining unit calculates an average of the gradation values of the eight adjacent pixels, and replaces the gradation value of the pixel with the average gradation value.

Further to the second embodiment of this invention; an inspection apparatus wherein in the false defect determining unit, if a difference between the maximum and the minimum of the gradation values of the eight adjacent pixels is more than a second threshold, the pixel is not regarded as a false defect.

In the third embodiment of this invention, an inspection method comprising; acquiring an optical image of an object to be inspected by irradiating the object with light, generating a reference image from design data of the object to be inspected,
comparing the optical image with the reference image, storing data of three lines acquired by a line sensor comprising a plurality of sensors linearly arranged in a row, calculating differences between a gradation value of a pixel and each gradation value of the eight pixels adjacent to the pixel are calculated for each pixel of the center line of the three lines, determining the pixel as a defect if all of the eight differences are more than a first predetermined threshold.

Further to the third embodiment of this invention; an inspection method wherein, if a difference between the maximum and the minimum of the gradation values of the eight adjacent pixels is more than a second threshold, the pixel is not regarded as a false defect.

Further to the third embodiment of this invention, an inspection method comprising; calculating an average of the gradation values of the eight adjacent pixels, and replacing the gradation value of the pixel with the average.

Further to the third embodiment of this invention; an inspection method wherein, if a difference between the maximum and the minimum of the gradation values of the eight adjacent pixels is more than a second threshold, the pixel is not regarded as a false defect.

Further to the third embodiment of this invention, an inspection method comprising; acquiring a second optical image of an image determined as a false defect by the line sensor, and replacing the optical image with the second optical image.

Further to the third embodiment of this invention, an inspection method wherein; if a difference between the maximum and the minimum of the gradation values of the eight adjacent pixels is more than a second threshold, the pixel is not regarded as a false defect.

BRIEF DESCRIPTION OF THE DRAWINGS

FIG. 2 is another example of gradation values of pixels according to the present embodiment as seen in FIG. 1.

FIG. 3 is another example of gradation values of pixels according to the present embodiment as seen in FIG. 1.

FIG. 10 is a diagram showing the gradation value every of pixel in the optical image.

FIG. 11 is a diagram showing the gradation value of the territory where white spot occurs.

DETAILED DESCRIPTION OF THE INVENTION

Figure 1:
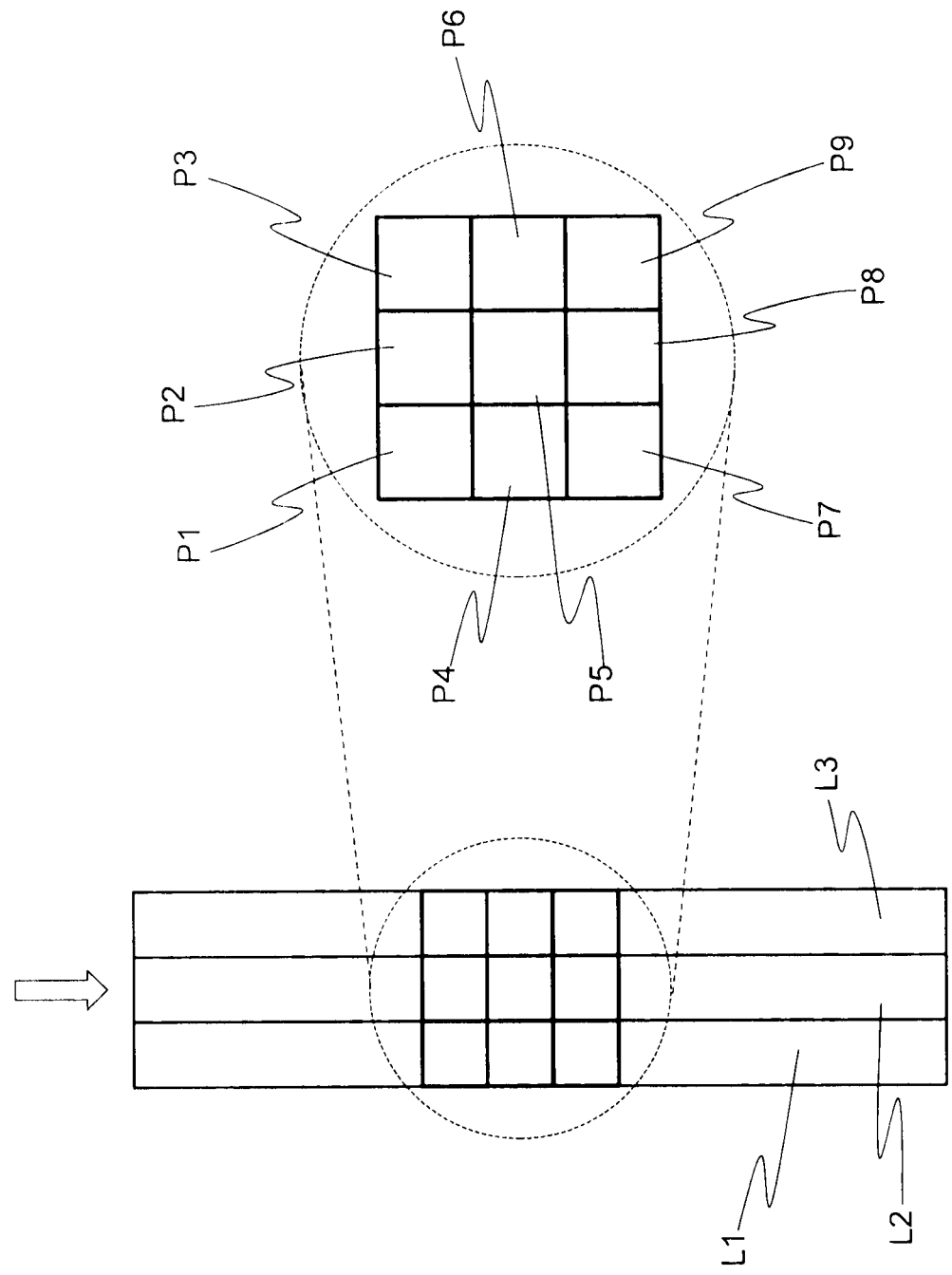
FIG. 1 is a diagram showing three lines to be stored as data in the present invention, a pixel of the center line and eight adjacent to pixels.

In an inspection process, light is emitted from a light source, and the object to be inspected is irradiated with this light through an optical system. The object to be inspected is mounted on a table, and this table is moved so that the emitted beam of light scans the surface of the object to be inspected. Light transmitted through or reflected from the object to be inspected is focused on an image sensor, thereby forming an image thereon. The optical image thus formed on the image sensor is sent to a comparing unit. The comparing unit compares the optical image with the reference image as a model, and if they are not identical, the object to be inspected is determined to have a defect.

Every pixel in the optical image is given any one of a gradation value from 0 to 225, thereby a writing pattern and a defect are displayed. Specifically an optical image and a reference image are formed, and then the difference of the gradation value of these is acquired to form a comparison image. If there is a difference of between the optical image and the reference image, the comparison image will be displayed, and the defect can be determined by viewing the comparison image.

FIG. 10 is an example showing gradation value of every pixel regarding an optical image acquired by an image sensor. When there is no pattern in the area shown in FIG.

10, all of the pixels should be the same value if there is no defect. In FIG. 10, the gradation value at the center position is 140, and then the value gradually reduces to 120, 110 and 100 outwardly to the adjacent to area. This indicates that there is a defect in this area.

If it is a true defect, as shown in FIG. 10, the gradation value would change gently in a range of several pixels. However a white spot as a false defect usually occurs in only one pixel of an optical image.

FIG. 11 is an example showing gradation values in an area where white spot is generated. In FIG. 11, only the center pixel has 200 as a gradation value, other pixels have 100. When white spot is generated, only a single pixel has a prominent value over other pixels. Therefore, it can be distinguished between a real defect generated in a range of several pixels such as FIG. 10. In the present embodiment, a defect generated in a single pixel is regarded as a white spot, and therefore should be removed. Thus a false defect can be removed from an optical image.

Specifically, data corresponding to 3 lines of optical data is acquired by an image sensor, in this case a line sensor, and is then stored in an inspection apparatus. The line sensor consists of a plurality of sensors linearly arranged in a row. The data is expressed by a gradation value of every pixel, each pixel is given any one of a gradation value from 0 to 255. The difference of a gradation value between one pixel and the gradation values of the eight neighboring pixels are calculated for each pixel of the center line, center line data being the centre line of the 3 lines stored in the inspection apparatus. When all of the eight pixels show differences more than the predetermined threshold, the center pixel will be determined as a false defect caused by a white spot.

FIG. 1 shows three lines (L1, L2, L3) that should be stored as a data, a pixel (P5) of the center line as an object (as above), and eight adjacent to pixels (P1, P2, P3, P4, P6, P7, P8, P9).

The gradation value of each pixel is defined as the following as shown in FIG. 1.

P1: a
P2: b
P3: c
P4: d
P5: e
P6: f
P7: g
P8: h
P9: i

When a relation between a, b, c, d, e, f, g, h and i is expressed by the following formulas, pixel P5 is determined as a white spot. X is a threshold set by the user.

a=100
b=110
c=110
d=100
e=150
f=100
g=100
h=110
i=110

FIG. 2 is a specific example of gradation values as seen in FIG. 1, and each value of a-i is as follows.

a=100
b=110
c=110
d=100
e=150
f=100
g=100
h=110
i=110

When the threshold X is equal to 30, differences between a gradation value of the pixel P5 and each gradation value of the other pixels are larger than the threshold. Therefore the pixel P5 is determined as a false defect by the white spot.

After the pixel P5 is determined as a false defect, a replacing method is performed to the value of the pixel P5. Specifically, an average of the gradation values of the eight adjacent to pixels (P1, P2, P3, P4, P6, P7, P8, P9) is calculated, and then the average is replaced with the gradation value of the pixel P5. For example, in FIG. 2, the average of the eight pixels (P1, P2, P3, P4, P6, P7, P8, P9) is equal 105 as follows.

(100+110+110+100+100+100+110+110)/8=105

The original gradation value 150 of the pixel P5 is replaced with the average 105. Thus a sensor data of the pixel P5 will not be regarded as a defect. That is, a false defect is removed from the optical image.

In the present embodiment, the following method can be performed instead of the above-mentioned replacing method. In this method a second optical image of a stripe determined as a false defect, is re-acquired again by the sensor, the second optical image then replaces the first optical image.

When the pixel P5 is initially determined as a white spot, the same stripe is scanned again by the line sensor. As the optical image data (the second optical image data) replaces the previous optical image data (the first image data), it can be determined if the sensor data of the pixel P5 is regarded as a defect. As the white spot generates randomly in time and space, the possibly that the white spot generates several times at the same position is extremely low. Therefore the differences between the gradation value of the pixel P5 and each gradation value of the adjacent to pixels would be at, or less than the threshold X, as a result of scanning the same stripe again.

Thus a defect generated in a pixel, is regarded as a white spot, and then this defect is removed. According to this method a false defect can be removed from an optical image without the necessity of a plurality of inspection processes.

In the following methods (1) and (2), pixel P5 will not be determined as a white spot even if the differences between the gradation value of the pixel P5 and each gradation value of the eight adjacent to values (P1, P2, P3, P4, P6, P7, P8, P9) are more than the threshold X.

(1) is a method wherein a difference between the maximum and the minimum in the gradation values of the eight pixels (P1, P2, P3, P4, P6, P7, P8, P9) is more than threshold Y. In this case, it is highly possible that the pixel P5 is on a pattern edge. The pattern edge is the boundary between an area which has a pattern and another area which doesn't have a pattern. Genuine defects are usually generated on the pattern edge. Therefore pixel P5 is not regarded as a white spot to prevent the real defect from being missed.

An example of pixel values is shown in FIG. 3. In FIG. 3, each value of a-i is as follows.

a=200
b=210
c=210
d=100
e=150
f=110
g=80
h=90
i=90

When the threshold X is equal to 30, the differences between the gradation value e of pixel P5 and each gradation value of the other pixels are larger than the threshold. When each gradation value of the eight pixels (P1, P2, P3, P4, P6, P7, P8, P9) is compared, the maximum is 210 and the minimum is 80, the difference of these is 130. If the threshold is equal 110, the difference between the maximum and the minimum is larger than the threshold. Therefore the pixel P5 will not be regarded as a white spot in this case.

(2) is a method wherein an optical image obtained by focusing light through an inspection object on a line sensor, and a second optical image obtained by focusing light reflected on the inspection object by an another line sensor are compared, and then both the pixel P5 of the optical image and the pixel P5 of the second optical image are determined as white spots at the same position. The light emitted through the inspection object is focused on a line sensor (first line sensor), and then the image data corresponding to three lines is stored. The light reflected on the inspection object is then focused on another line sensor (second line sensor) and the image data corresponding to these three lines is stored. In each pixel of a center line in three lines acquired by the first line sensor, differences between a gradation value of a pixel and each gradation value of the pixels adjacent to the pixel are calculated. Also in each pixel of a center line of three lines acquired by the second line sensor, differences between a gradation value of a pixel and each gradation value of the pixels adjacent to the pixel are calculated. When all of these differences are more than the threshold X at the same pixel, this center pixel will not be determined to be a false defect. In the present embodiment, a line sensor can include both roles as the first line sensor and the second line sensor without two separate line sensors.

As white spot is usually generated randomly in time and space, the possibility that a white spot will generate several times in the same position is extremely low. Therefore, in FIG. 1, when a gradation value suggested to be a white spot, in pixel P5 is acquired of the transparent image and pixel P5 of the reflected image at the same position, the pixel P5 will not be determined as a white spot.

By including the above steps (1) and (2) as cases for exclusion during determination it is possible to decrease the possibility that a real defect will be regarded as a false defect.

Figure 4:
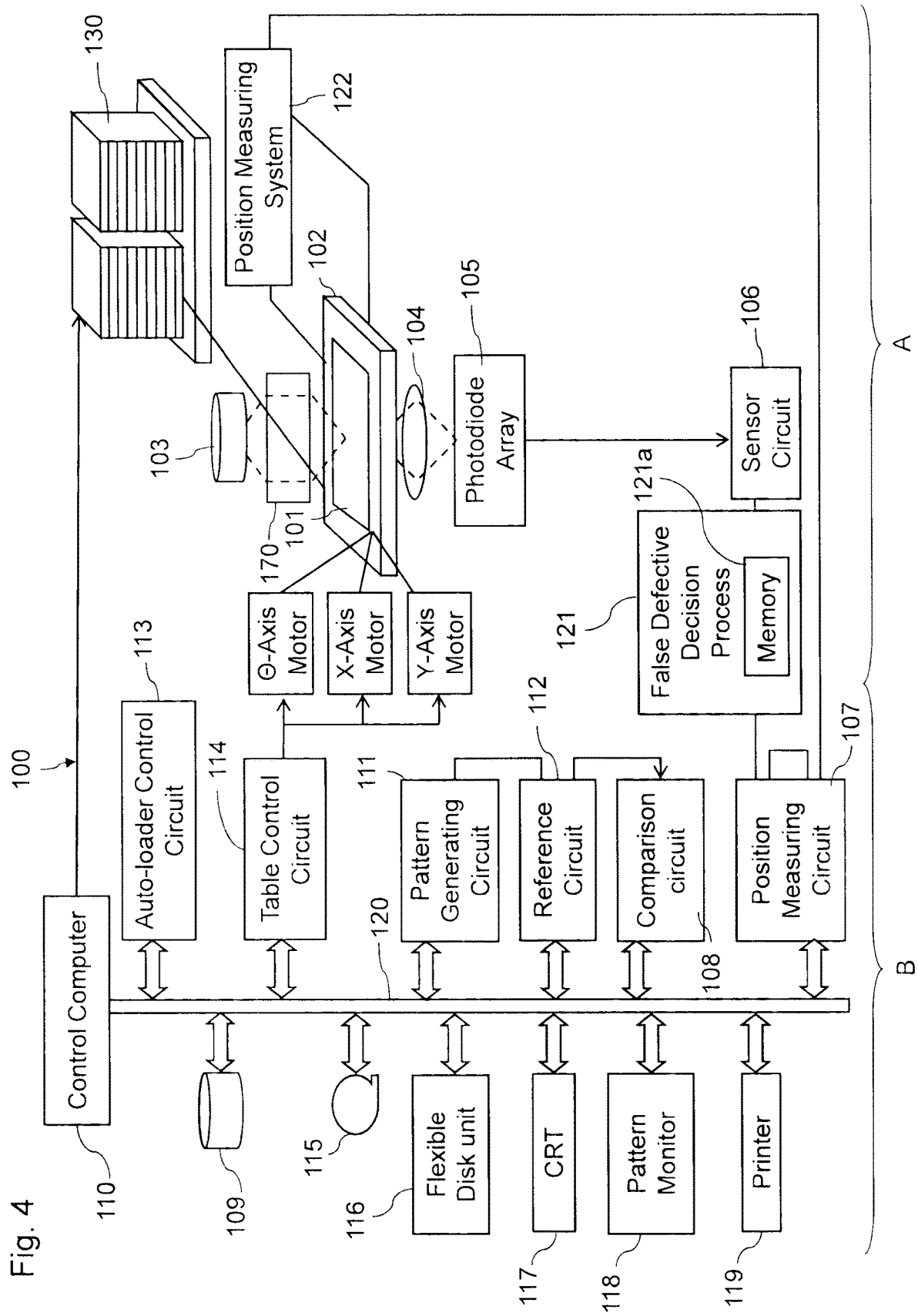
FIG. 4 is a diagram showing the configuration of an inspection system according to the present embodiment.

FIG. 4 is a diagram showing the configuration of an inspection system 100 according to the present embodiment. In the present embodiment, a mask is used as the inspection object but a wafer can be used instead.

As shown in FIG. 4, the inspection apparatus 100 includes an optical image acquiring unit A and a control unit B.

The optical image acquiring unit A includes a light source 103, a XYθ table 102 movable in the horizontal direction (X and Y directions) and in the rotation direction (θ direction), an optical illumination system 170 serving as a transmission illumination system, an enlarging optical system 104, a photodiode array 105, a sensor circuit 106, false defect determining unit 121, a laser length measuring system 122, and an autoloader 130.

In the control unit B, a control computer 110 which controls the entire inspection apparatus 100 is connected through a bus 120 (serving as a data transmission path) to a position measuring circuit 107, a comparing circuit 108, a reference circuit 112, a pattern generating circuit 111, an autoloader control unit 113, a table control circuit 114, a disk storage unit 109 serving as storage units, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, for e.g., step motors.

Design pattern data used as reference data in database inspection is stored in the disk storage unit 109. This data is read out and sent to the pattern generating circuit 111 when required in the course of the inspection process. The pattern generating circuit 111 converts the design pattern data into image data (or design pixel data). This image data is then sent to the reference circuit 112 for generating of reference data.

It should be noted that the inspection apparatus of the present embodiment may include, in addition to the components shown in FIG. 4 described above, other known components required to inspect masks.

Figure 5:
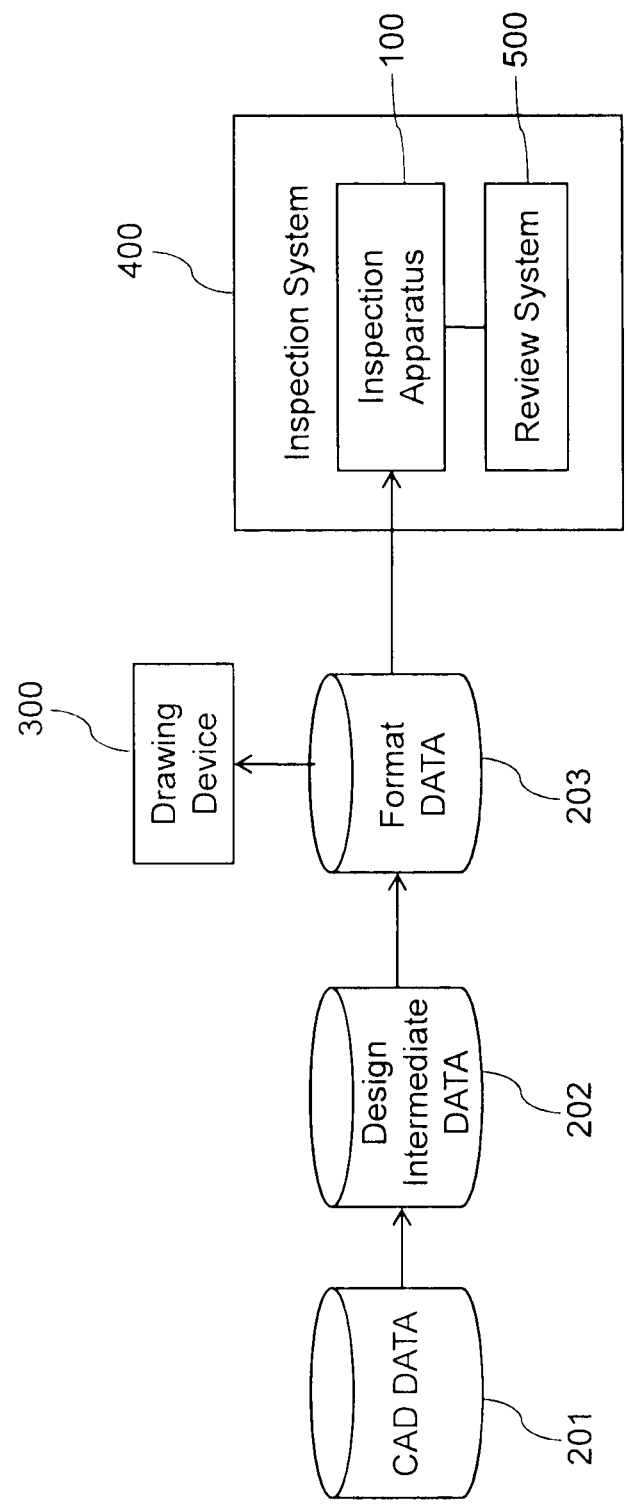
FIG. 5 is a schematic diagram showing a flow of data according to the present embodiment.

FIG. 5 is a schematic diagram showing a flow of data according to the present embodiment.

As shown in FIG. 5, CAD data 201 prepared by the designer (or user) is converted to intermediate design data 202 in a hierarchical format. The intermediate design data 202 includes data of the pattern formed on the mask created for each layer. It should be noted that, generally, writing apparatus 300 are not adapted to be able to directly read intermediate design data 202. That is, each manufacturer of a writing apparatus 300 uses different format data. Therefore, intermediate design data 202 is converted, for each layer, to format data 203 in a format specific to the writing apparatus 300 used, and this format data 203 is input to the writing apparatus 300. The inspection apparatus is not adapted to be able to directly read the intermediate design data 202. Therefore, the intermediate design data 202 is converted to a format data compatible with the writing apparatus 300, and then the converted data is input to the inspection apparatus. The intermediate design data 202 is converted to a format data in a format specific to the inspection apparatus 100, and then the converted data is input to the inspection apparatus 100.

Figure 6:
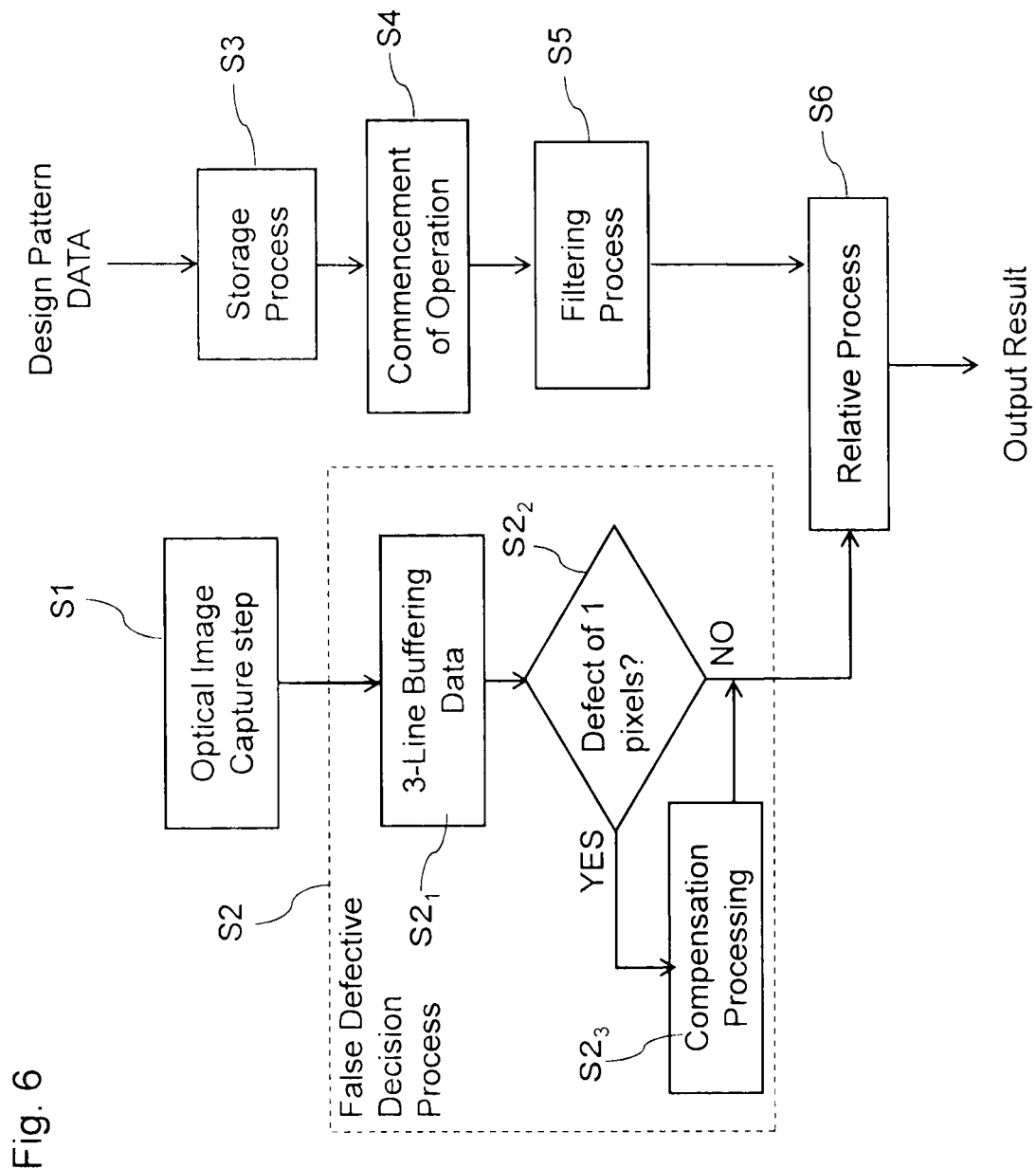
FIG. 6 is a flowchart showing an inspection process according to the present embodiment.

FIG. 6 is a flowchart showing an inspection process.

As shown in FIG. 6, this inspection process includes an optical image acquire step (S1), false defective decision processing process (S2), a design pattern data storage step (S3), a pattern generating step (S4), a filtering step (S5), and a comparing step (S6), where the pattern generating step and the filtering step together form a reference image data generating step.

<Optical Image Acquire Step>

At the optical image acquire step S1, the optical image acquire unit A shown in FIG. 4 acquires an optical image (acquisition data) of a photomask 101. The optical image is an image of a mask on which graphics are written, based on the graphic data in the design pattern. The detailed method of acquiring this optical image is as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the illumination optical system 170 and irradiates on the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown).

Figure 7:
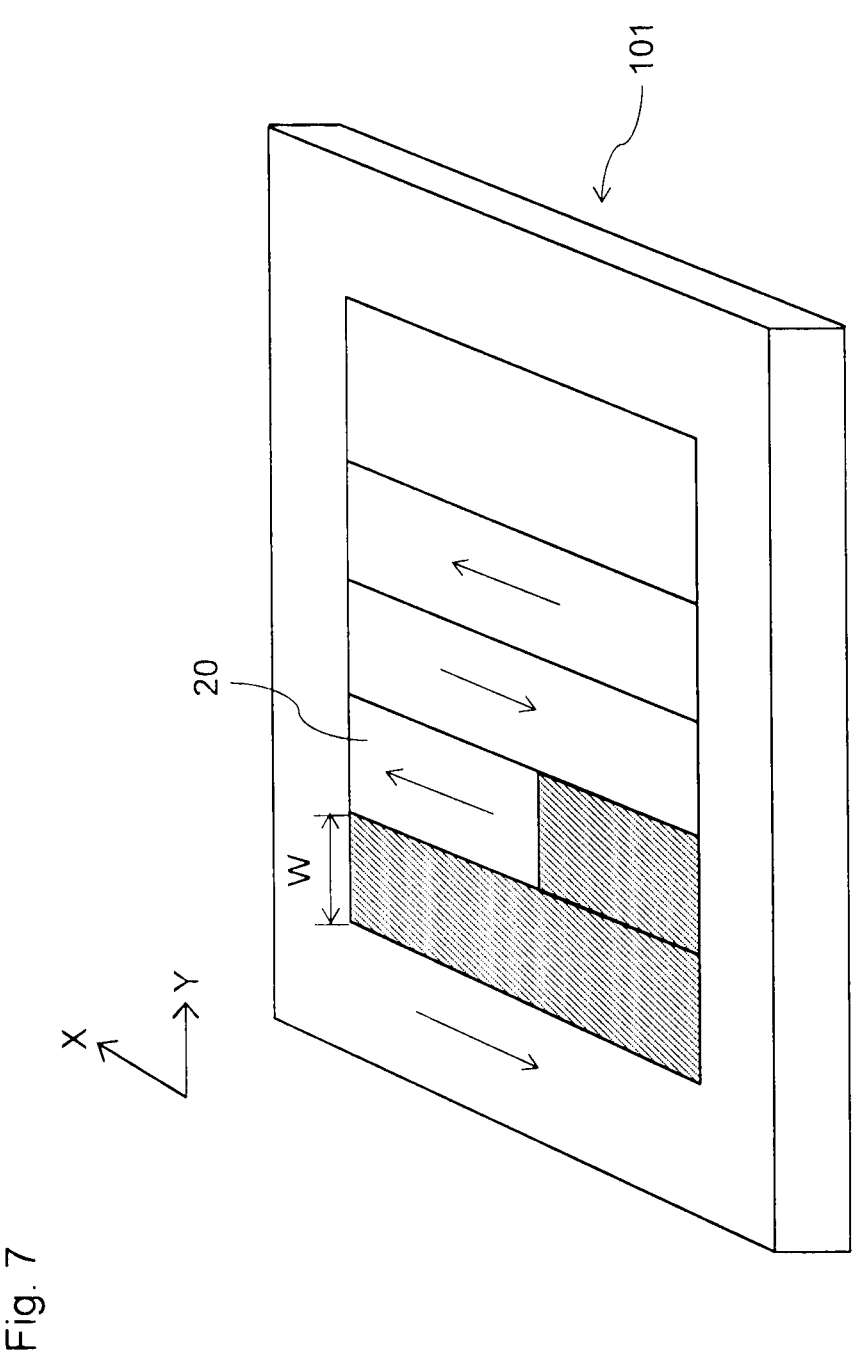
FIG. 7 is a diagram illustrating the way in which an optical image is acquired.

FIG. 7 is a diagram illustrating the way in which an optical image is acquired.

The inspection area is divided into a plurality of strip-shaped inspection stripes 20 by imaginary lines running in the X direction, where the width of each inspection stripe 20 in the Y direction is equal to the scan width W, as shown in FIG. 7. The movement of the XYθ table 102 in FIG. 4 is controlled so that each inspection stripe 20 is continuously scanned in the negative or positive X direction with light to acquire an image of the inspection stripe. At that time, the photodiode array 105 continuously generates an image (of each inspection stripe 20) having a width corresponding to the scan width W, as shown in FIG. 7. After acquiring an image of the first inspection stripe 20 by scanning it in the negative X direction, the second inspection stripe 20 is continuously scanned in the positive (i.e., opposite) X direction to acquire an image of a width corresponding to the scan width W. When the third inspection stripe 20 is acquired, in the opposite direction to the direction for acquiring the image in the second inspection stripe 20, that is, the XYθ table 102 moves in the direction for acquiring the image in the first inspection stripe 20. This method of continuously acquiring an image of one inspection stripe 20 after another reduces the processing time.

The pattern image formed on the photodiode array 105 as shown in FIG. 4 is photoelectrically converted by the photodiode array 105 and then converted from analog to digital (A-D conversion) by the sensor circuit 106. The photodiode array 105 includes sensors, in the present embodiment, linear sensors having CCD cameras arranged in one line could be used. This line sensor may be, for e.g., TDI (Time Delay Integration) sensors. Thus, the pattern on the photomask 101 is imaged by these TDI sensors while the XYθ table 102 is continuously moved in the positive or negative X direction. It should be noted that the light source 103, the enlarging optical system 104, the photodiode array 105, and the sensor circuit 106 together form a high power optical inspection apparatus.

The XYθ table 102 can be moved in the X and Y directions and rotated in a θ direction by a drive system, such as a 3-axis (X-Y-θ) motor driven by the table control circuit 114 under the control of the control computer 110. These X-, Y-, and θ-axis motors may be, for e.g., step motors. The position of the XYθ table 102 is measured by the laser length measuring system 122, and the optical image measurement data is sent to the position measuring circuit 107. Further, the photomask 101 is automatically loaded onto the XYθ table 102 from the autoloader 130 driven by the autoloader control unit 113 and upon completion of the inspection the photomask 101 is automatically retrieved from the XYθ table 102.

<Step of Determining a False Defect>

In FIG. 4, acquired data (an optical image) is sent from the sensor circuit 106 to the false defect determining unit 121. The false defect determining unit 121 performs a process of determining a false defect (S2), see FIG. 6.

In the present embodiment, data of three lines is stored in the memory 121a as an optical image acquired by a line sensor ($S2_1$).

The data stored in the memory 121a is expressed by gradation values every pixel. Each pixel is given any one of gradation values from 0 to 255. In the present embodiment, differences between a gradation value of a pixel and each gradation value of the eight pixels adjacent to the pixel are calculated for each pixel of the center line, center line data being the centre line of the 3 lines, this calculated data is then stored.

Next, $S2_2$ determines if there is a defect generated in one pixel. Specifically, differences between a gradation value of a pixel and each gradation value of the pixels adjacent to the pixel are calculated, and then in S22, a determination is performed to determine if all of the eight differences are more than a predetermined threshold. When all of these differences are more than the threshold, the pixel is determined to be a defect generated in one pixel, that is, a false defect caused by a white spot. However the pixel will not be determined as the white spot in the following methods (1) and (2).

(1) is a method wherein a difference between the maximum and the minimum in the gradation values of the eight pixels (P1, P2, P3, P4, P6, P7, P8, P9) is more than threshold Y.
(2) is a method wherein a first optical image obtained by focusing light through an inspection object on a line sensor, and a second optical image obtained by focusing light reflected on the inspection object by another line sensor are compared, and then both the pixel P5 of the first optical image and the pixel P5 of the second optical image are determined as white spots at the same position.

When there is a defect that is generated in a pixel in $S2_2$, a replacement method is performed in $S2_3$. That is, an average of all the gradation values of the eight adjacent to pixels is calculated, and then the average is replaces the gradation value of the pixel. Thus, the sensor data of the pixel will not be regarded as a defect. Data removed the false defect from the optical image is sent to the comparing circuit 108, this data shows the gradation of brightness of each pixel, this data may be 8-bit unsigned data, as one possible example. The data showing the position of the photomask 101 on the XYθ table 102 is output from the position circuit 107 and sent to the comparing circuit 108.

When there are no defects that are generated in one pixel in $S2_2$, the optical image acquired in S1 is sent to the comparing circuit 108.

<Storage Step>

In the storage step S3 as shown in FIG. 6 the design pattern data that was used to form the pattern on the photomask 101 is stored in the magnetic disk unit 109 serving as a storage unit.

The designed pattern includes pattern features each consisting of basic features such as rectangles and triangles. The magnetic disk unit 109 stores feature data indicating the shape, size, and position of each pattern feature, specifically, e.g., information such as the coordinates of the reference position of each feature, the length of its sides, and a shape code (or identifier) identifying the type of shape such as a rectangle or triangle.

Further, a group of pattern features, defined in an area of approximately a few tens of micrometers square is referred to as a "cluster" or "cell". It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

<Pattern Generating Step>

In the pattern generating step S4 as shown in FIG. 6, the pattern generating circuit 111 (shown in FIG. 4) reads design pattern data of the photomask 101 from the magnetic disk unit 109 through the control computer 110 and converts it into 2-bit or other multiple-bit image data (reference image data). This image data is sent to the reference image generating circuit 112.

Specifically, upon reading the design pattern data (serving as feature data), the pattern generating circuit 111 expands it to produce data of each pattern feature and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit reference image data of the design pattern segment in each grid element. By using the produced reference image data, the pattern generating circuit 111 calculates the design pattern occupancy in each grid element (corresponding to a sensor pixel). This pattern occupancy in each pixel represents the pixel value.

<Filtering Step>

At the filtering step S5 in FIG. 6, after receiving the reference image data (i.e., image data of the pattern), the reference image generating circuit 112 performs appropriate filtering on the data.

Figure 8:
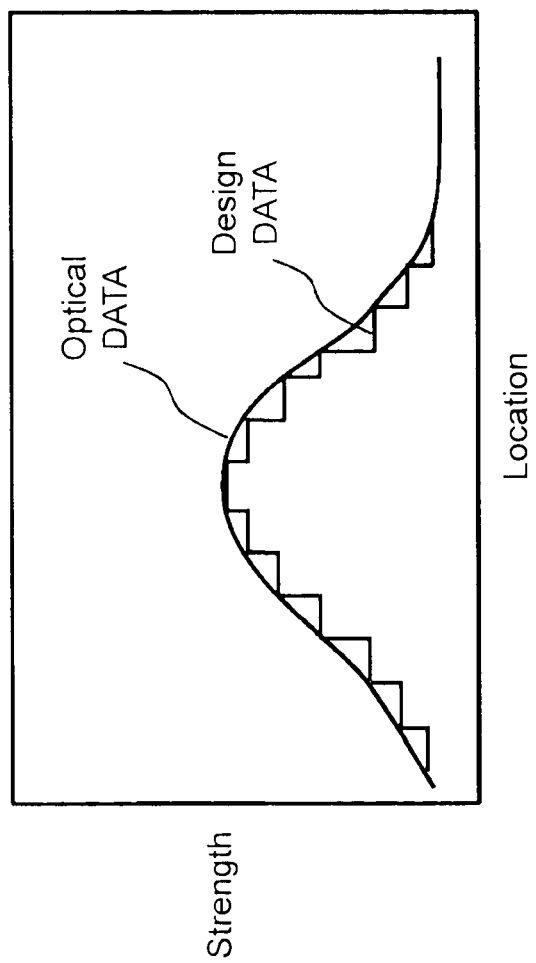
FIG. 8 is a diagram illustrating the filtering according to the present embodiment.

FIG. 8 is a diagram illustrating the filtering.

The optical image, i.e. the acquired data, output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the reference image data corresponding to the optical image is digital data consisting of digital values representing the intensity (or gray scale) of each point of the image, this reference image data may be filtered to match the "blurred" optical image, or optical image measurement data. In this way, a reference image to be compared with the optical image is produced.

<Comparing Step>

As described above, the optical image data from the false defect determining unit 121 is sent to the comparing circuit 108. This data includes both the optical image data from the sensor circuit 106 and the data removed the false defect from the optical image data. The pattern generating circuit 111 converts the design pattern data into image data (or design pixel data). This image data is then sent to the reference circuit 112 for generating of reference data and then sent to the comparing circuit 108.

In the comparing circuit 108, the optical image which is sent from the false defect determining unit 121 and the reference image which is formed in the reference circuit 112, are compared in accordance with an appropriate algorithm, and if the difference of these is more than the predetermined value, the mask is determined to have a defect. In this case, it retains the coordinate, the optical image and the reference image used as the basis for the defective decision.

According to the present embodiment when a defect generated in a pixel is regarded as a white spot the defect is removed from an optical image data. Thus false defects can be removed and accuracy of determination in the comparing circuit 108 can be improved.

The inspection system 400 according to the present embodiment consists of an inspection apparatus 100 and a review apparatus 500 for reviewing the inspection result (FIG. 5). The operator performs a review based on the above inspection result by the review apparatus 500. In the review process, the operator determines whether a pattern defect found in the inspection can be tolerated. According to the present embodiment, a defect generated in one pixel regarded as a white spot is removed from an optical image data. As false defects can be decreased, the processing time in the review can also be decreased.

Figure 9:
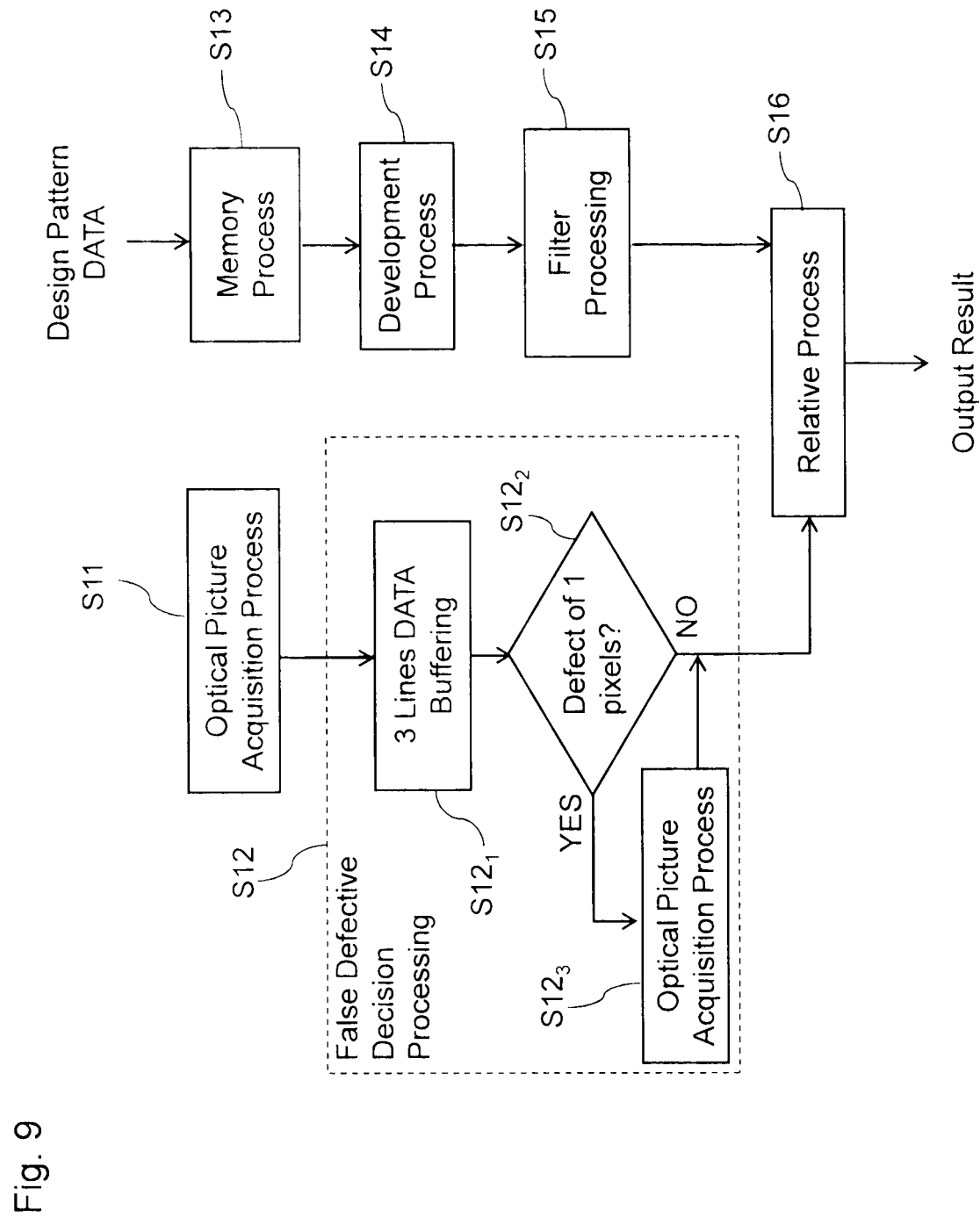
FIG. 9 is a flowchart showing another example of the inspection process according to the present embodiment.

FIG. 9 is a flowchart showing another example of the inspection process. Steps (S11, S13-S16), except the false defect determining step (S12), are not mentioned in this example, because these steps are same as steps (S1, S3-S6) mentioned in FIG. 6.

In FIG. 4, the acquiring data input from the sensor circuit 106 is sent to the false defect determining unit 121. The false defect determining step (S12) shown in FIG. 9 is performed in the false defect determining unit 121.

In the present embodiment, the data corresponding to three lines in the optical image acquired by the line sensor is stored in the memory 121a (S12$_1$).

The data stored in the memory 121a is expressed by the gradation value of every pixel. Each pixel is given any one of the gradation values from 0 to 255. In the present embodiment, differences between a gradation value of a pixel and each gradation value of the eight pixels adjacent to the pixel are calculated in each pixel of the center line in stored data.

In S12$_2$ a determination is made to determine if there is a defect generated in a pixel. Specifically, differences between a gradation value of a pixel and each gradation value of the pixels adjacent to the pixel are calculated. A determination is then made as to whether the eight differences in the pixels are more than a predetermined threshold. When all of these differences are more than the threshold, the pixel is determined as a defect, that is, a false defect caused by white spot. However the pixel will not be determined as the white spot in the following methods (1) and (2).

(1) is a method wherein a difference between the maximum and the minimum in the gradation values of the eight pixels (P1, P2, P3, P4, P6, P7, P8, P9) is more than threshold Y.

2) is a method wherein a first optical image obtained by focusing light through an inspection object on a line sensor, and a second optical image obtained by focusing light reflected on the inspection object by another line sensor are compared, and then both the pixel P5 of the first optical image and the pixel P5 of the second optical image are determined as white spots at the same position.

When there is a defect generated in a pixel in S12$_2$, the optical image acquiring step S12$_3$ is performed, this step is the same as in the S11. In S12$_2$, the same stripe as the stripe that is determined whether to be a false defect or not, is scanned again by the line sensor. As white spot is usually generated randomly in time and space, the possibility that a white spot will generate several times in the same position is extremely low. Therefore by scanning again at the same position, the differences between the gradation value of the pixel and each gradation value of the adjacent to pixels would be less than the threshold. The image data acquired by scanning again replaces the previous image data, and then the new gradation value can be applied, thus the sensor data of the pixel P5 will not be regarded as a defect. That is, the data in which the false defect is excluded from the optical image is sent to the comparing circuit 108. This date may be unsigned 8-bit data, as one possible example, is expressed gradation values of brightness of every pixels. The data showing the position of the photomask 101 on the XYθ table 102 is output from the position circuit 107 and sent to the comparing circuit 108.

When there are no defects that are generated in a pixel in $S12_2$, the optical image acquired in S11 is sent to the comparing circuit 108.

As the above mentioned, according to the present embodiment, a defect that is generated in a pixel is regarded as a white spot, and then the defect is removed from the optical image data. Thus the false defects can be removed from the optical image without requiring a plurality of inspection processes. Therefore, the burden on the operator can be decreased in the review step and accuracy of the inspection can be increased.

The present invention is not limited to the above-mentioned embodiments and may be utilized without departing from the spirit and scope of the present invention.

For example, the die-to-database method is mentioned in the present invention, but also the die-to-die method can be used as a defect inspection method.

The above description of the invention has not specified apparatus constructions, control methods, etc. which are not essential to the description of the invention, since any suitable apparatus constructions, control methods, etc, can be employed to implement the invention. Further, the scope of this invention encompasses all pattern inspection apparatus and pattern inspection methods employing the elements of the invention and variations thereof which can be designed by those skilled in the art.

What is claimed is:

1. An inspection method comprising:
    acquiring a first optical image of an object to be inspected by irradiating the object with light;
    generating a reference image from design data of the object to be inspected;
    storing data of three lines acquired by a line sensor comprising a plurality of sensors linearly arranged in a row;
    calculating eight differences between a gradation value of a target pixel and each gradation value of eight pixels adjacent to the target pixel for each pixel of the center line of the three lines;
    determining the target pixel as a false defect by determining that all of the eight differences are more than a first predetermined threshold and a difference between a maximum and a minimum of the gradation values of the eight pixels adjacent to the target pixel is less than or equal to a second threshold;
    generating a corrected optical image by acquiring a second optical image of the object positioned on at least the center line including the target pixel and replacing the gradation value of the target pixel determined to be a false defect with a gradation value of the target pixel obtained from the second optical image;
    comparing the corrected optical image with the reference image; and
    outputting the comparison result.

2. An inspection method comprising:
    acquiring first and second optical images of an object to be inspected by irradiating the object with light, the first optical image obtained by focusing light through an inspection object on a first line sensor comprising a plurality of sensors linearly arranged in a row, and the second optical image obtained by focusing light reflected from the inspection object by a second line sensor comprising a plurality of sensors linearly arranged in a row;
    generating a reference image from design data of the object to be inspected;
    storing first data of three lines acquired by the first line sensor and second data of three lines acquired by the second line sensor;
    calculating eight differences between a gradation value of a target pixel and each gradation value of eight pixels adjacent to the target pixel for each pixel of the center line of the three lines corresponding to the first data, and eight differences between a gradation value of the target pixel and each gradation value of the eight pixels adjacent to the target pixel for each pixel of the center line of the three lines corresponding to the second data;
    determining the target pixel as a false defect by determining that all of the eight differences corresponding to one of the first and second data are more than a predetermined threshold and all of the eight differences corresponding to the other of the first and second data are less than or equal to a predetermined threshold;
    generating a corrected optical image by acquiring a third optical image of the object positioned on at least the center line including the target pixel and replacing the gradation value of the target pixel determined to be a false defect with a gradation value of the target pixel obtained from the third optical image;
    comparing the corrected optical image with the reference image; and
    outputting the comparison result.

* * * * *